US010166039B2

(12) United States Patent
Gunday et al.

(10) Patent No.: US 10,166,039 B2
(45) Date of Patent: Jan. 1, 2019

(54) VIEWING TROCAR

(71) Applicants: Erhan H. Gunday, Great Neck, NY (US); Lawrence J. Gerrans, San Anselmo, CA (US)

(72) Inventors: Erhan H. Gunday, Great Neck, NY (US); Lawrence J. Gerrans, San Anselmo, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 975 days.

(21) Appl. No.: 13/867,729

(22) Filed: Apr. 22, 2013

(65) Prior Publication Data

US 2013/0282041 A1 Oct. 24, 2013

Related U.S. Application Data

(60) Provisional application No. 61/636,259, filed on Apr. 20, 2012.

(51) Int. Cl.
*A61B 1/05* (2006.01)
*A61B 17/32* (2006.01)
*A61B 1/00* (2006.01)
*A61B 17/34* (2006.01)
*A61B 90/00* (2016.01)

(52) U.S. Cl.
CPC .. *A61B 17/320016* (2013.01); *A61B 1/00183* (2013.01); *A61B 17/3421* (2013.01); *A61B 90/37* (2016.02); *A61B 1/05* (2013.01); *A61B 2090/371* (2016.02); *A61B 2090/3784* (2016.02)

(58) Field of Classification Search
CPC ... A61B 1/00188; A61B 1/04; A61B 1/00096; A61B 1/042; A61B 1/05; A61B 19/52; A61B 19/5202; A61B 19/5212; A61B 1/00016; A61B 1/00034; A61B 1/00183; A61B 1/00193
USPC .......................................... 600/112, 113, 160
See application file for complete search history.

(56) References Cited

U.S. PATENT DOCUMENTS

| | | | |
|---|---|---|---|
| 5,305,121 A * | 4/1994 | Moll | A61B 1/05 348/45 |
| 5,380,291 A | 1/1995 | Kaali | |
| 5,467,762 A | 11/1995 | Sauer et al. | |
| 5,591,192 A | 1/1997 | Privitera et al. | |
| 5,674,184 A | 10/1997 | Hassler, Jr. | |
| 5,797,944 A | 8/1998 | Nobles et al. | |
| 6,066,090 A * | 5/2000 | Yoon | A61B 1/00045 600/113 |
| 6,269,379 B1 * | 7/2001 | Hiyama | G06T 3/40 |
| 7,601,119 B2 * | 10/2009 | Shahinian | A61B 1/00087 600/104 |

(Continued)

*Primary Examiner* — John P Leubecker
(74) *Attorney, Agent, or Firm* — Forge IP, PLLC

(57) ABSTRACT

A viewing trocar assembly is provided including a tubular body having a proximal end and a distal end, and an opening provided at the distal end, and at least one imaging device positioned on an outer wall of the distal end of the tubular body, wherein the at least one imaging device is adjacent to the outer wall of the distal end of the tubular body when in an inactivated position, and wherein the at least one imaging device is extended further away from the outer wall of the distal end of the tubular body when in an activated position than when in the inactivated position.

37 Claims, 7 Drawing Sheets

(56) References Cited

U.S. PATENT DOCUMENTS

| | | | |
|---|---|---|---|
| 7,751,870 B2* | 7/2010 | Whitman | A61B 1/313 600/104 |
| 8,197,399 B2* | 6/2012 | Bayer | A61B 1/0005 348/72 |
| 8,277,373 B2* | 10/2012 | Maahs | A61B 1/0008 600/104 |
| 8,529,612 B2* | 9/2013 | Singh | A61F 7/123 128/898 |
| 8,602,980 B2* | 12/2013 | Bassan | A61B 1/00009 600/129 |
| 8,827,891 B2* | 9/2014 | Roberts | A61B 17/00234 600/204 |
| 9,271,637 B2* | 3/2016 | Farr | A61B 1/00096 |
| 9,295,375 B2* | 3/2016 | Shahinian | A61B 1/045 |
| 2002/0049367 A1* | 4/2002 | Irion | A61B 1/00183 600/173 |
| 2002/0188204 A1* | 12/2002 | McNamara | A61B 1/00082 600/478 |
| 2005/0080318 A1* | 4/2005 | Squicciarini | A61B 1/00087 600/114 |
| 2005/0234296 A1* | 10/2005 | Saadat | A61B 1/0008 600/129 |
| 2006/0252994 A1* | 11/2006 | Ratnakar | A61B 1/00179 600/173 |
| 2007/0255100 A1* | 11/2007 | Barlow | A61B 1/0005 600/114 |
| 2008/0275298 A1* | 11/2008 | Ratnakar | A61B 1/00105 600/109 |
| 2010/0081875 A1* | 4/2010 | Fowler | A61B 1/00149 600/114 |
| 2010/0249512 A1* | 9/2010 | McKinley | A61B 17/3421 600/160 |
| 2011/0160530 A1* | 6/2011 | Ratnakar | A61B 1/0005 600/104 |
| 2011/0160535 A1* | 6/2011 | Bayer et al. | 600/109 |
| 2011/0160740 A1* | 6/2011 | Makower | A61B 17/24 606/115 |
| 2011/0306832 A1* | 12/2011 | Bassan | A61B 1/00009 600/109 |
| 2013/0345503 A1* | 12/2013 | Friedrich | A61B 1/00016 600/103 |
| 2014/0107417 A1* | 4/2014 | McKinley | A61B 17/3421 600/112 |

* cited by examiner

VIEWING TROCAR

FIELD OF THE INVENTION

The present invention relates to medical devices for penetrating bodily tissues. More specifically, the present invention relates to an improved trocar assembly having enhanced visualization capabilities.

BACKGROUND OF THE INVENTION

In recent years, minimally invasive surgery has become much more common for performing various types of surgical procedures. This type of surgery has tremendous advantages over traditional "open" surgery in that it does not require a large incision, typically in a person's abdomen, to perform the surgery—something that has revolutionized patient care.

Surgical trocars are commonly used to perform minimally invasive surgery. They are deployed as a means of introduction for cameras and various surgical instruments, such as scissors, graspers, etc., to perform surgery on a patient. A trocar is a medical instrument, typically with a sharply pointed end, often three-sided, that is used with a hollow cylinder or cannula to penetrate walls or bodily cavities. Trocars are also commonly used to introduce ports in the abdomen, such as during laparoscopic surgery. Often, the combined trocar and cannula are referred to as a trocar. The trocar is often passed inside a cannula, and functions as a portal for the subsequent placement of other devices, such as a chest drain, intravenous cannula, etc.

As the insertion of a trocar, even with the skilled selection of a penetration site, involves a risk of damaging blood vessels, internal organs and other interior structures at the insertion site, there have been several attempts in the prior art to improve the imaging capabilities of trocar assemblies. Examples of such prior art imaging trocar systems are described, for example, in U.S. Pat. No. 5,797,944 to Nobles et al., U.S. Pat. No. 5,674,184 to Hassler, Jr., U.S. Pat. No. 5,467,762 to Sauer et al., U.S. Pat. No. 5,591,192 to Privitera et al., and U.S. Pat. No. 5,380,291 to Kaali. These systems typically include a piercing member having an imaging device positioned at the distal tip of the piercing member. While these systems provide improved visualization of bodily tissues during the trocar insertion, they are not useful after the trocar is positioned inside a patient's body and the piercing member with the imaging device is withdrawn from the patient.

There are several prior art trocar systems that provide some visualization capabilities after the trocar has been inserted into a bodily cavity. One of such systems disclosed in US 2011/0160535 to Bayer et al. provides a disposable access port for use in laparoscopic or endoscopic procedures, including a cannula with an embedded camera and a trocar device disposed in the cannula lumen. Once the cannula with the trocar is inserted into a patient's body, the trocar is withdrawn, which urges the camera out of the cannula.

However, these systems still suffer from significant drawbacks. For example, there is usually a single imaging device rigidly affixed on an outer wall of the trocar that is capable of providing only a narrow image of an adjacent tissue site. Also, the prior art imaging devices are not maneuverable and adjustable once positioned inside a patient's body, thus providing limited imaging capabilities.

Therefore, there is a need for a trocar assembly that overcomes the shortcomings of the prior art systems and provides enhanced imaging capabilities after the trocar is inserted and positioned inside the patient's body.

SUMMARY OF THE INVENTION

It is, therefore, an object of the present invention to provide a new and improved trocar assembly that overcomes the above discussed shortcomings of known trocar systems.

In order to overcome the deficiencies of the prior art and to achieve at least some of the objects and advantages listed, a viewing trocar assembly is provided including a tubular body having a proximal end and a distal end, and an opening provided at the distal end, and at least one imaging device positioned on an outer wall of the distal end of the tubular body, wherein the at least one imaging device is adjacent to the outer wall of the distal end of said tubular body when in an inactivated position, and wherein the at least one imaging device is extended further away from the outer wall of the distal end of said tubular body when in an activated position than when in the inactivated position.

In certain embodiments, the viewing trocar assembly further includes at least one connector attaching the at least one imaging device to the outer wall of the tubular member. In some of these embodiments, the at least one connector is extended away from the outer wall of the distal end of the tubular body at an angle when the at least one imaging device is in the activated position. In certain of these embodiments, the angle is in the range of from about five degrees to about one hundred and eighty degrees. In further of these embodiments, the at least one connector comprises shape memory material. In certain of these embodiments, the at least one connector comprises nitinol material.

In some embodiments, the at least one imaging device comprises three imaging devices positioned on the outer wall of the tubular body. The certain of these embodiments, the three imaging devices are positioned circumferentially at a substantially equal distance from each other. In some of these embodiments, image data generated by each of the three imaging devices is displayed to a user as separate images. In other embodiments, image data generated by each of the three imaging devices is displayed to a user as a single combined image.

In certain embodiments, the viewing trocar assembly further includes an outer housing movably positioned over the tubular body. In some these embodiments, the at least one imaging device is positioned in the activated position by moving the outer housing in a proximal direction. In other of these embodiments, the at least one imaging device is positioned in the activated position by moving the tubular body in a distal direction. In further of these embodiments, the viewing trocar assembly further includes at least one imaging device positioned in an outer wall of the outer housing.

In certain embodiments, the distal end of the tubular body comprises a piercing device.

In some embodiments, the viewing trocar assembly further includes a piercing member movably disposed inside the tubular body and extending out of the distal end of the tubular body when in an activated position.

In some cases, the at least one imaging device comprises a CMOS device. In further embodiments, the at least one imaging device comprises a CCD device.

In certain embodiments, the at least one imaging device comprises at least one illumination device generating light for illuminating surrounding tissue. In some of these embodiments, the at least one illumination device comprises at least one light emitting diode.

In some embodiments, the viewing trocar assembly further includes a processor coupled to and receiving image data from the at least one imaging device. In certain of these embodiments, the viewing trocar assembly further includes a display coupled to the processor and displaying image data received from the at least one imaging device. In additional embodiments, the image data generated by the at least one imaging device is wirelessly transmitted to the processor. In further embodiments, the image data generated by the at least one imaging device is transmitted to the processor via a cable.

In certain embodiments, the viewing trocar assembly further includes a power source providing electrical power to the viewing trocar assembly.

In some cases, the viewing trocar assembly further has a storage coupled to the viewing trocar assembly for storing image data generated by the at least one imaging device.

In certain advantageous embodiments, the viewing trocar assembly further includes at least one imaging marker positioned on the outer wall of the tubular member.

In some embodiments, the viewing trocar assembly further includes a control device for manipulation of the viewing trocar assembly by a user.

A method of performing a medical procedure is also provided including the steps of inserting a viewing trocar assembly into a patient's body, the viewing trocar assembly comprising a tubular body having a proximal end and a distal end, and an opening provided at the distal end, and at least one imaging device positioned on an outer wall of the distal end of the tubular body, and moving the at least one imaging device from an inactivated position, in which the at least one imaging device is adjacent to the outer wall of the distal end of said tubular body, to an activated position, in which the at least one imaging device is extended further away from the outer wall of the distal end of the tubular body than when in the inactivated position, to visualize surrounding tissue.

In certain embodiments, the viewing trocar assembly further includes an outer housing movably disposed over the tubular body, and the step of moving the at least one imaging device between the inactivated and activated positions comprises longitudinally moving the tubular body and the outer housing relative one another.

In some embodiments, the method further includes the step of transmitting image data from the at least one imaging device to a display coupled to the viewing trocar assembly for display to a user.

In certain embodiments, the viewing trocar assembly further has at least one illumination device, and he method further includes the step of illuminating surrounding tissue via the at least one illumination device.

In some cases, the method further includes the step of inserting at least one medical instrument into the patient's body via a lumen of the tubular body.

In certain embodiments, the method further includes the step of rotationally moving the tubular body.

In some embodiments, the step of inserting the viewing trocar assembly into the patient's body includes the step of piercing bodily tissue with a piercing device positioned at the distal end of the tubular body.

Other objects of the invention and its particular features and advantages will become more apparent from consideration of the following drawings and accompanying detailed description.

DETAILED DESCRIPTION OF THE INVENTION

Figure 1:
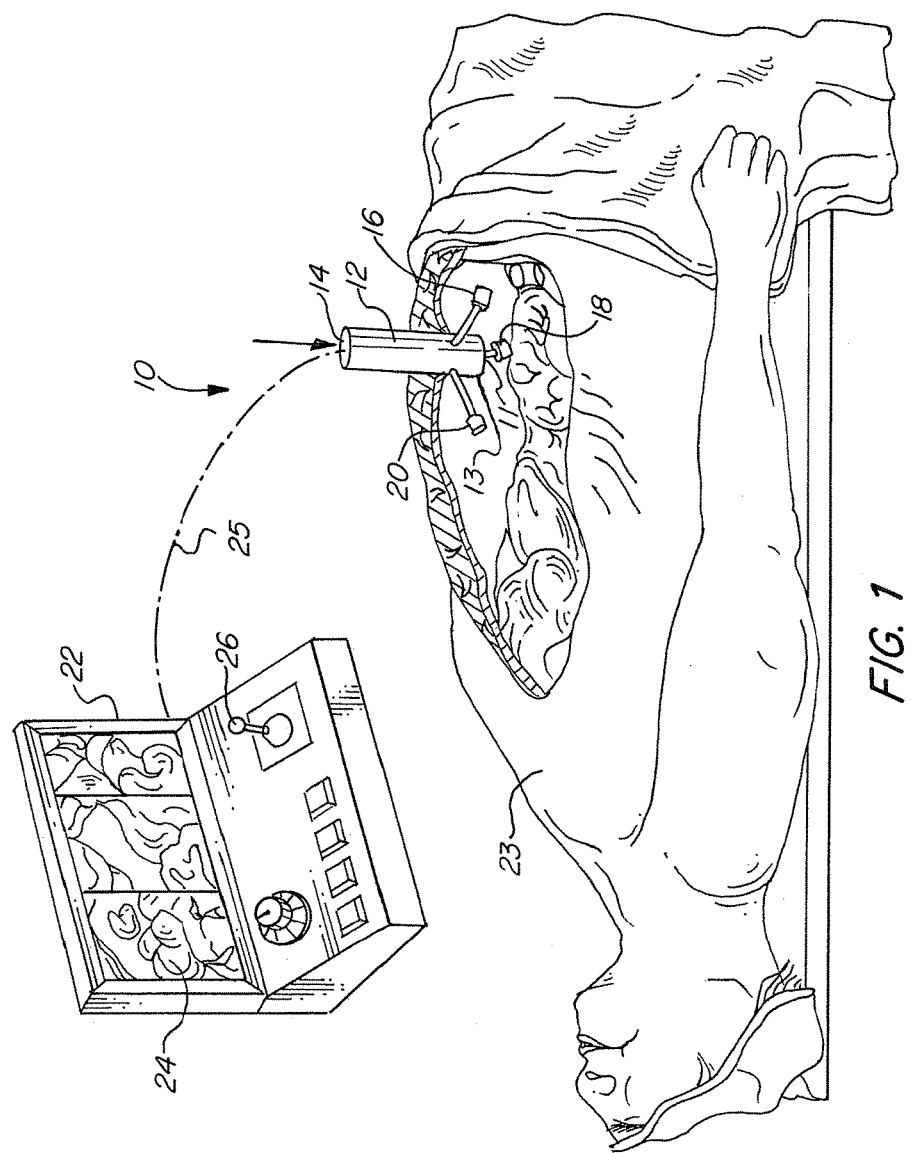
FIG. 1 is a schematic view of the viewing trocar assembly in accordance with the invention being operated inside a patient's body.

The basic components of one embodiment of a viewing trocar assembly in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The viewing trocar assembly of the present invention may be used in a wide variety of minimally invasive surgical and diagnostic procedures. It may be used to introduce any type of surgical, diagnostic, or imaging devices into a patient's body at various locations.

One exemplary embodiment of a viewing trocar assembly of the present invention is shown in FIG. 1. The trocar assembly (10) includes a tubular body (12) with a lumen (14) that terminates at an opening (11) at a distal end (13) of the body. The tubular body (12) functions as a working channel that allows a surgeon to introduce various medical devices into a patient's body during various medical procedures. The trocar body is made with any suitable biocompatible material that is preferably axially rigid, such as hard plastic, stainless steel, glass, or plexiglass. The diameter and length of the tubular body may be adjusted depending on a particular medical procedure being carried out.

The trocar (10) further includes at least one imaging device positioned on the outer wall of the trocar body (12). In the exemplary embodiment shown in FIG. 1, three imaging devices (16, 18, 20) are positioned at equal distances from each other around the circumference of the trocar body (12). Each of the three imaging devices (16, 18, 20) is capable of capturing an image at a 120 degree angle. Such design makes it possible for a surgeon to obtain a complete 360 degree image of the surrounding tissue. It should be noted, however, that any number of imaging devices may be used without departing from the spirit of the invention. Also, the imaging devices may be positioned at different locations and distances along the trocar body (12).

Any number of suitable imaging devices may be used in accordance with the present invention. In some advantageous embodiments, the imaging device is a fiber optic image bundle. Two separate fiber optic bundles—an incoherent fiber bundle for illumination and a coherent fiber bundle for image—can also be used in accordance with the present invention. It should be noted that a suitable image sensor (e.g. CCD or CMOS) can be positioned at the tip of the imaging devices (16, 18, 20), eliminating the need for a coherent imaging fiber bundle, thus increasing the image quality and reducing cost. It should also be noted that other sources of illumination, such as light emitting diodes, can be employed and positioned adjacent to the imaging devices, or at any other suitable location on the trocar body (12), to illuminate the surrounding areas of bodily cavities into which the trocar assembly (10) is introduced. In some embodiments, the imaging devices may be ultrasonic devices capable of providing ultrasonic images to monitor the location of the trocar assembly (10) inside a patient's body.

The trocar assembly (10) is connected to a central control unit (22). The central control unit (22) preferably includes an image display or a monitor (24) for viewing an image of the surgical site provided by the imaging devices (16, 18, 20) positioned on the trocar body (12). The monitor (24) may be capable is providing simultaneous images from each of the three separate imaging devices (16, 18, 20), as shown in FIG. 1. Alternatively, the images from the imaging devices may be integrated into one image that provides the surgeon with a 360 degree view of the surgical site.

The central control unit (22) also includes at least one manually operatable manipulator (26) coupled to the trocar assembly (10) for controlling and manipulating the trocar assembly by the surgeon. Any type of suitable manipulator device may be used in accordance with the present invention. When using the central control unit (22), the surgeon may sit in a chair in front of the central control unit (22), position his/her eyes in front of the monitor (24), and operate one or more manipulators (26), while observing the surgical site on the monitor (24). In other embodiments, the manipulator (26) may be a portable remote control device, such that the surgeon can move about the room.

The central control unit (22) further includes a processor for processing imaging data received from the imaging devices positioned on the trocar assembly (10). Any suitable type of processor may be used in accordance with the invention. The processor is also used to send control signals from the central control unit (22) to the trocar assembly (10) for controlling the trocar by the surgeon.

The trocar assembly (10), positioned inside a patient (23), may be remotely controlled using the central control unit (22) (e.g. surgical workstation), which may be located away from an operating table, such as at a surgeon's station within an operating room, in a control room within a hospital, or at another facility. The central control unit (22) is connected to the trocar assembly (10) by cables or through wireless connection (25) and may be attached to a hospital local network and/or a remote network such as the Internet. A controller may be positioned on a proximal end of the trocar assembly for receiving control signals from the central control unit and for transmitting imaging data from the imaging devices to the central control unit.

Figure 6:
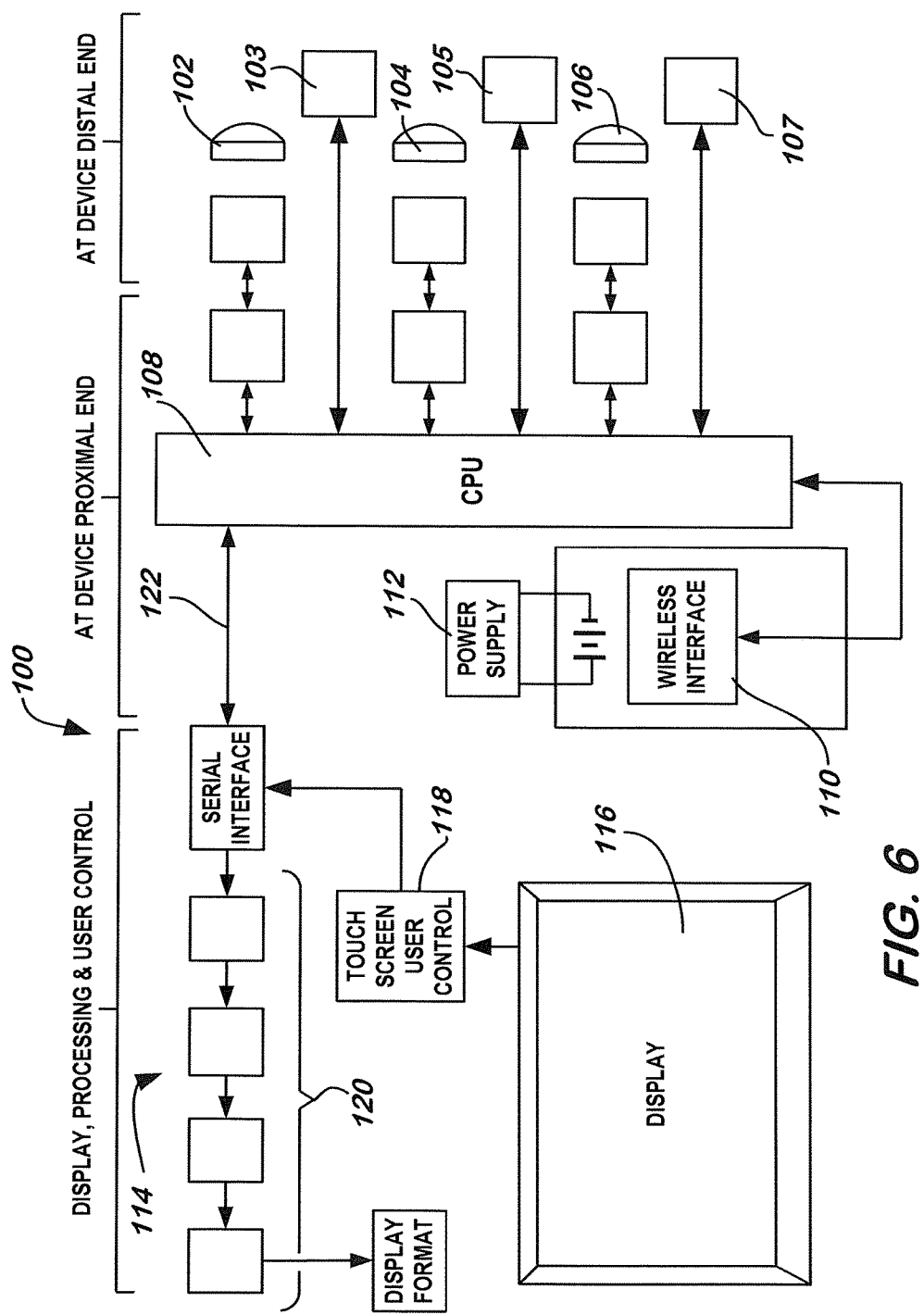
FIG. 6 is a schematic diagram showing the components of the viewing trocar assembly of FIG. 1.

FIG. 6 is a schematic block diagram illustrating components and operation of one exemplary embodiment of the trocar assembly in accordance with the invention. In this embodiment, the trocar assembly (100) includes three imaging devices (102, 104, 106) positioned at the distal end of the trocar. Each of the imaging devices includes an optics component, such as an objective lens, a sensor, and an analog to digital converter. Additionally, light sources (103, 105, 107) are positioned in proximity to each imaging device. The imaging devices are coupled to a control unit (108) positioned at the proximal end of the trocar. The control unit performs various functions, including processing of imaging data received from the imaging devices, transmitting the imaging data to a display for viewing by a surgeon, and receiving control signals from a user control interface. The control unit (108) is connected to a wireless interface (110) and a power supply (112) preferably positioned in close proximity to the trocar. The power supply (112) supplies necessary power to the trocar. The wireless interface (110) is used to wirelessly transmit data to and from the control unit (108).

Figure 7:
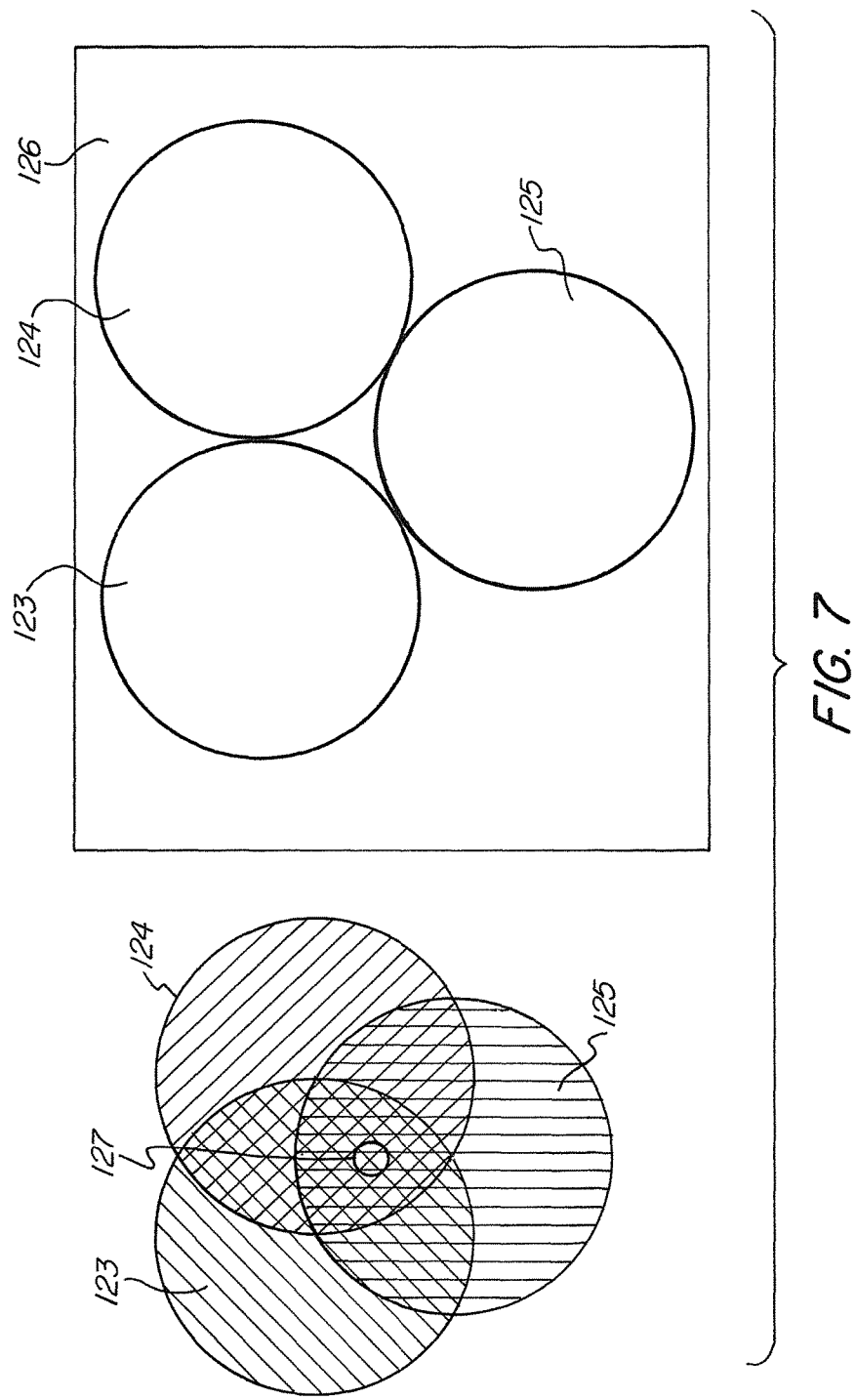
FIG. 7 is a schematic view of image data captured by the viewing trocar assembly of FIG. 1.

The trocar assembly (100) further includes a central control station (114) positioned away from the operating table. The central control station (114) includes a display (116), a user interface (118), and various image processing components (120). The central control station (114) may be connected to the trocar by cables (122) or through wireless connection. The imaging data received from the control unit (108) positioned on the trocar is processed by the image processing components (120) and transmitted to the display (116) for viewing by the surgeon. In some embodiments, such as an embodiment shown in FIG. 7, the images (123, 124, 125) from each of the imaging devices are displayed simultaneously on the display screen (126). Each of the images preferably captures an approximately 120 degree view of the target tissue site, such that the surgeon can obtain a full 360 degree view (127) of the tissue site from the combined images (123, 124, 125).

The central control station (114) further includes a user interface (118) for control and manipulation of the trocar assembly (100) by the surgeon. In some embodiments, the user interface (118) is a touch screen user interface that may be formed as a part of the display (116). The user interface (118) is connected to the control unit (108) for transmitting control signals to the trocar.

Figure 2:
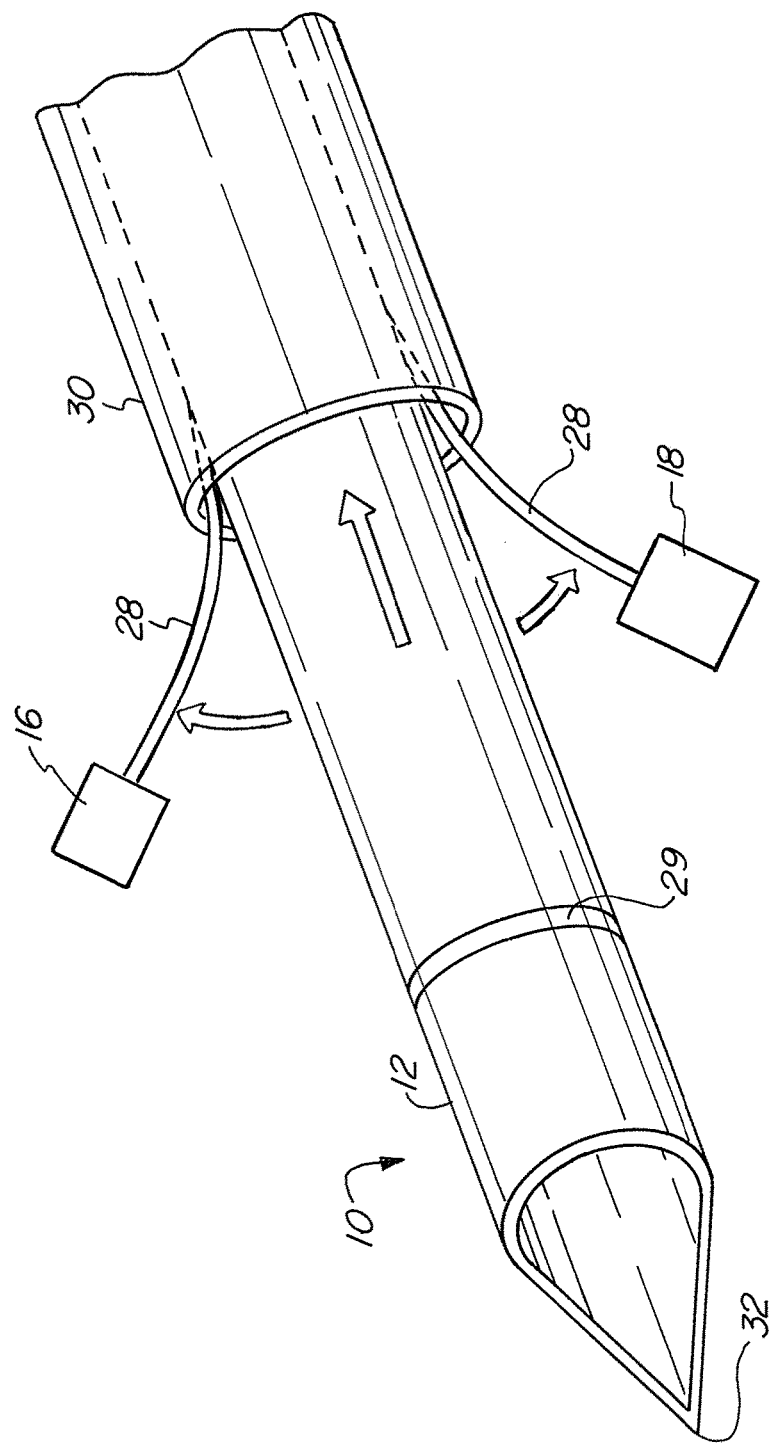
FIG. 2 is an enlarged perspective view of a distal end of the viewing trocar assembly of FIG. 1, shown in an activated position.

In some advantageous embodiments, the imaging devices are coupled to the trocar body (12) via an attachment mechanism. For example, as shown in FIG. 2, the imaging devices (16, 18) are positioned on flexible rods (28), which are attached to the trocar body (12). The rods (28) are preferably made with any type of flexible, but resilient material that is capable of being temporary deformed. In some advantageous embodiments, the rods (28) are made with nitinol material. Nitinol is a metal alloy of nickel and titanium, with the two elements mixed in roughly equal atomic percentages. Nitinol alloys exhibit a so-called superelasticity property, which is particularly useful to the application of this material in the present invention. Superelasticity is the ability of the nitinol alloys to undergo deformation and then recover its original, undeformed shape. Nitinol exhibits a superior elasticity compared to ordinary metals, approximately 10-30 times that of ordinary metal.

Figure 3:
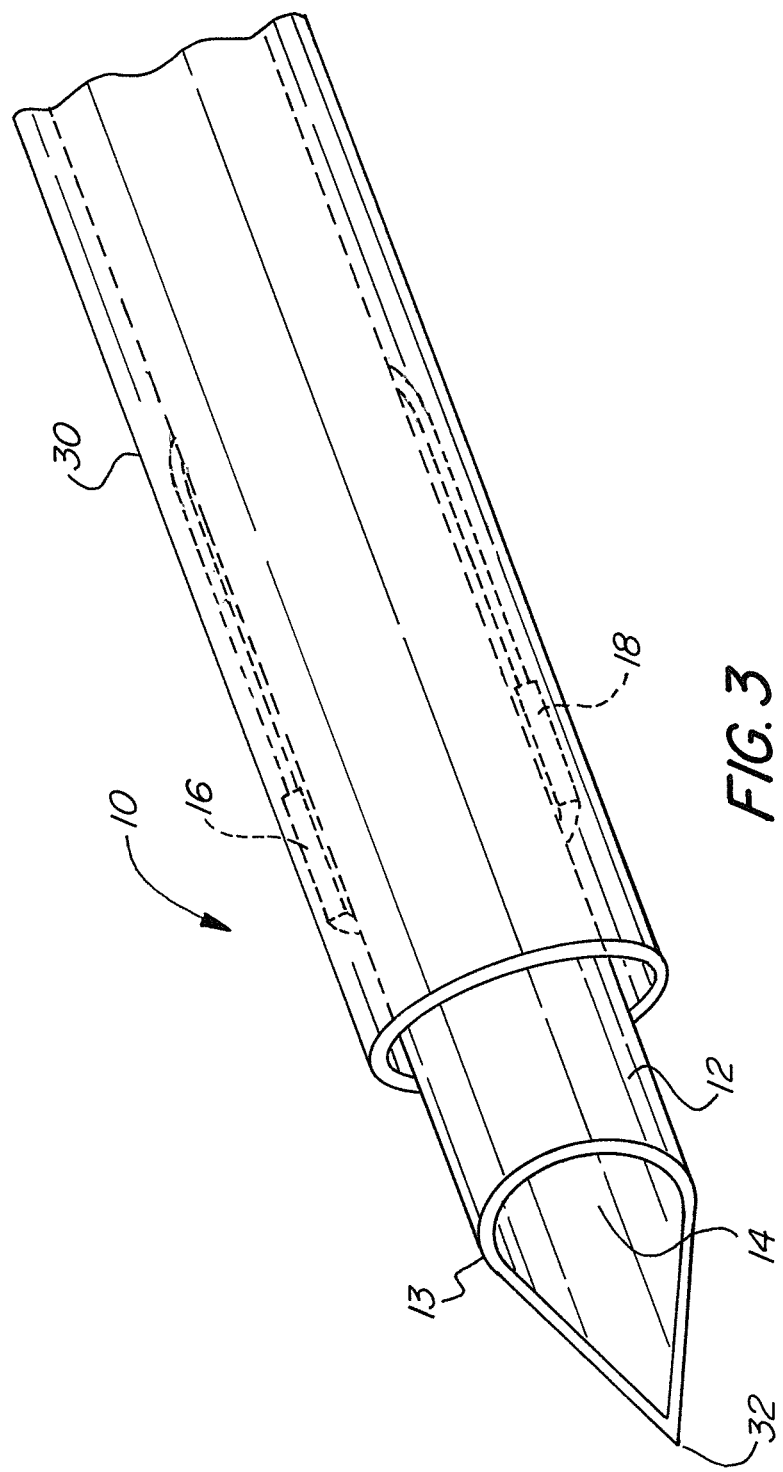
FIG. 3 is an enlarged perspective view of the distal end of the viewing trocar assembly of FIG. 1, shown in an inactivated position.

Before the insertion of the trocar assembly (10) into a patient's body, an outer housing (30) is positioned over the trocar body (12), as shown in FIG. 3. When the outer housing (30) is moved over the trocar body (12), it forces the rods (28) to bend closer to the trocar body such that the outer housing (30) covers the imaging devices (16, 18). This way, the trocar assembly (10) may be safely introduced in the patient's body.

After the trocar assembly (10) is inserted into a bodily cavity, the outer housing (30) is removed from the trocar body (12). This causes the flexible rods (28) to recover their original undeformed shape, as shown in FIG. 2, wherein the imaging devices (16, 18) extend away from the trocar body (12) at an angle. The angle is chosen based on a particular application and imaging capabilities desired.

In some advantageous embodiments, the distal end (13) of the trocar body (12) has a pointed shape with a sharp edge, as shown in FIGS. 2 and 3. This pointed sharp edge (32) acts as a piercing device for puncturing bodily tissues when the trocar assembly (10) is introduced into a patient's body. It should be noted that the shape of the distal end (13) shown in these figures is only exemplary, and that any other shape suitable for puncturing tissues may be used in accordance with the present invention.

Figure 4:
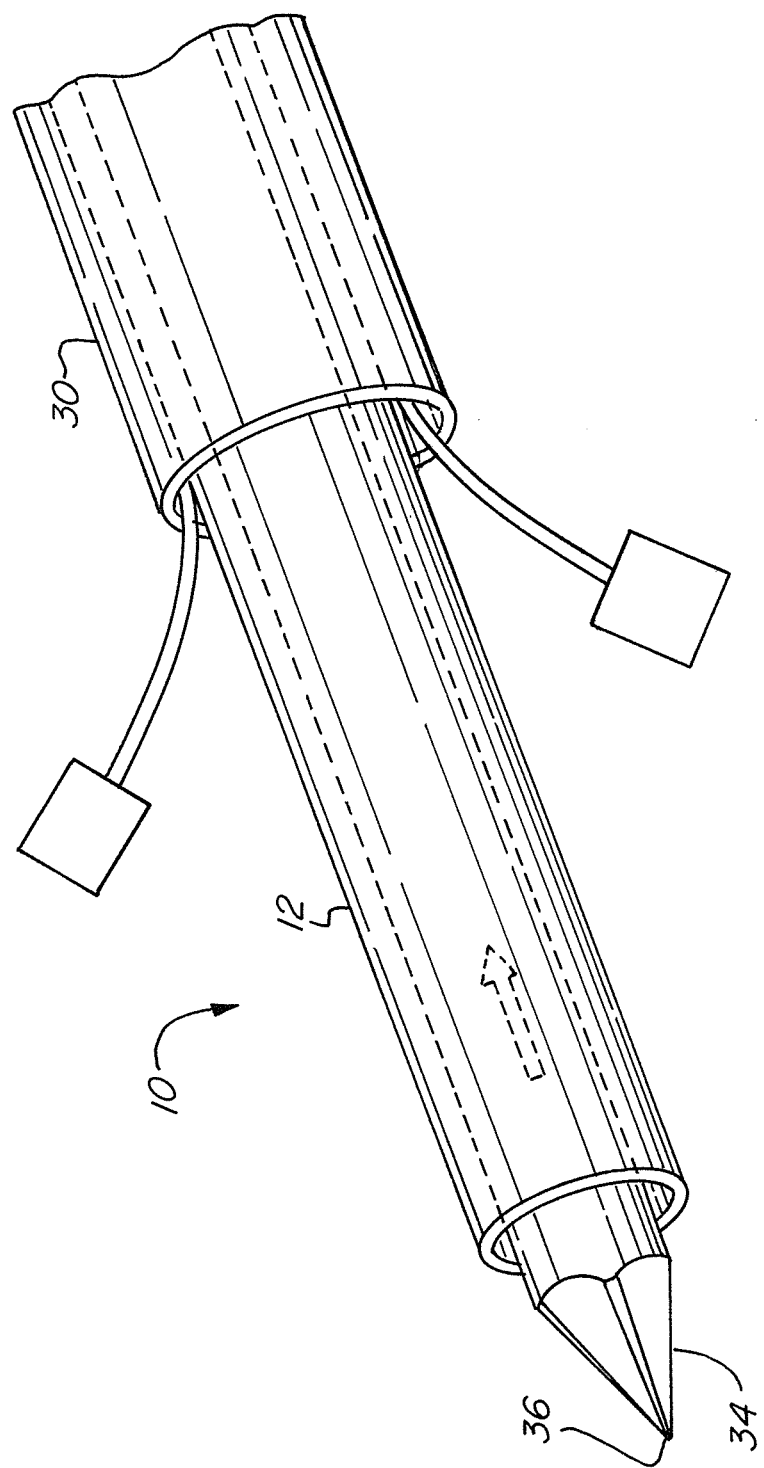
FIG. 4 is an enlarged perspective view of a distal end of the viewing trocar assembly of FIG. 1, showing a piercing member.

In other advantageous embodiments, such as an embodiment illustrated in FIG. 4, the trocar assembly (10) may further include a separate piercing device (34). The piercing device (34) has a rod line shape with a sharp pointed distal end (36) that is capable of cutting through layers of skin and tissue. An outer diameter of the piercing device (34) is smaller than the inner diameter of the trocar body (12), such that it can be inserted into the lumen (14) of the trocar body and is movable therein. The piercing device (34) is made with any suitable biologically compatible material, such as stainless steel, and is preferably inflexible such that it will not bend when encountering bodily tissue, but instead will pierce through it. In some embodiments, the distal end (36) of the piercing device (34) may include an imaging device to assist the surgeon in safe introduction of the piercing device into a patient's body. In some of these embodiments, the distal end (36) of the piercing device (34) may be fabricated from light transparent material to enable imaging of the insertion site by the surgeon. In further embodiments, the distal end (36) may include a light source to illuminate the surrounding tissue during the insertion of the trocar.

Figure 5:
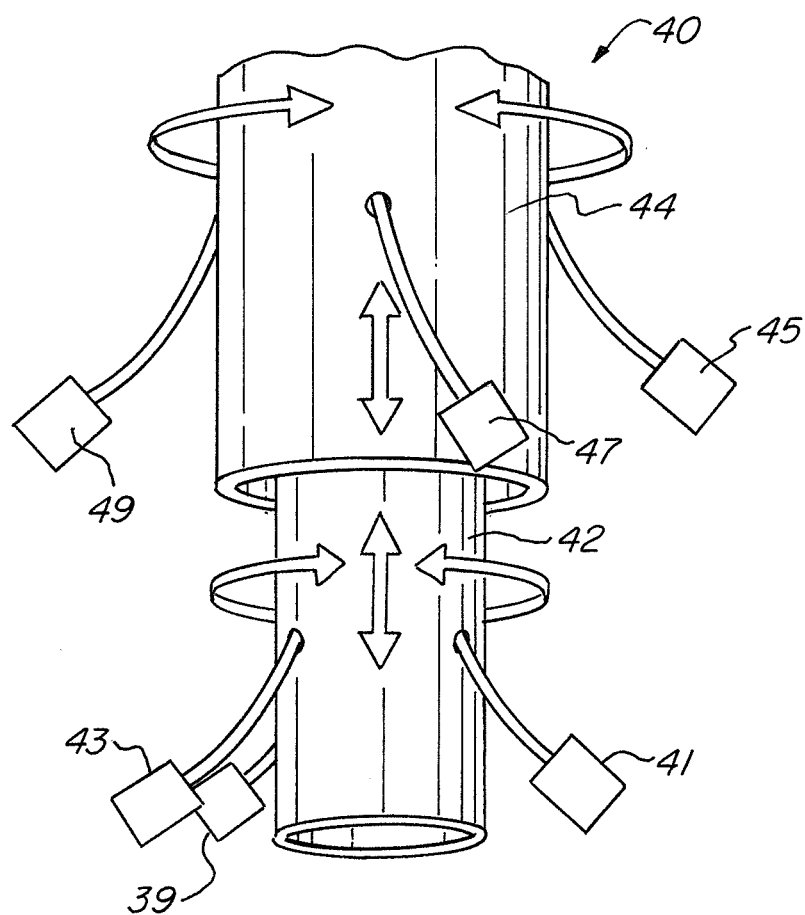
FIG. 5 is an enlarged perspective view of a distal end of the viewing trocar assembly of FIG. 1.

FIG. 5 illustrates another exemplary embodiment of the viewing trocar assembly of the present invention. In this embodiment, the trocar assembly (40) includes an inner trocar body (42) and an outer trocar body (44), provided in a telescopic arrangement. An inner diameter on the outer trocar body (44) is larger than an outer diameter of the inner trocar body (42), such that the outer body slides over the inner body. Each of the inner trocar body (42) and the outer trocar body (44) has at least one imaging device positioned thereon. In the embodiment shown in FIG. 5, the inner trocar body (42) has three imaging devices (39, 41, 43) positioned thereon, and the outer trocar body (44) also has three imaging devices (45, 47, 49) coupled thereto. It should be noted, however, that any number of imaging devices may be used with the inner and outer trocar bodies.

Before the trocar assembly (40) is introduced into a patient's body, the outer trocar body (44) is positioned over the inner trocar body (42), and the outer trocar body is covered with an outer housing, such that the imaging devices are housed therein. This facilitates a safe insertion of the trocar assembly. Once the trocar assembly is positioned in a bodily cavity, the outer housing is withdrawn, and the inner trocar body (42) is extended out of the distal end of the outer trocar body (44), such that the imaging devices splay outwards, as shown in FIG. 5.

Both the inner and outer trocar bodies (42, 44) are movable along their longitudinal axis such that they can be positioned at different locations inside a patient's body. For example, the imaging devices (45, 47, 49) on the outer trocar body (44) may be used to provide a general image of a tissue site. Then, the inner trocar body (42) is extended out of the outer trocar body and closer to the target site, and one of the imaging devices (39, 41, 43) on the inner body is used to zoom in on the target tissue to provide a more detailed image thereof. Further, the inner and outer trocar bodies (42, 44) are rotatable around their longitudinal axis. Such arrangement allows the surgeon to obtain a more complete panoramic view of surrounding tissue and use the imaging devices (39, 41, 43) on the inner trocar body (42) to focus in on specific portions of the target site.

In certain advantageous embodiments, such as illustrated in FIG. 2, the viewing trocar (10) includes imaging markers (29), such as radio opaque rings, positioned on the outer surface of the trocar body (12). One or more imaging markers may be used, and the markers may be positioned at or near the ends of the trocar body, or at any position along the length of the body. Such markers can be selected and appropriately positioned in order to reflect or block the relevant waves of various imaging modalities (e.g., x-ray) in order to allow the use of such modalities to assist with the precise positioning of the trocar assembly (10) inside a patient's body.

In some embodiments, the trocar assembly (10) also includes at least one illumination device to illuminate the surrounding tissue to provide a better visualization of the same. The illumination devices may be positioned at any suitable location along the trocar body (12). In some advantageous embodiments, the illumination devices are positioned adjacent the imaging devices. Any suitable type of illumination device known in the art may be used in accordance with the present invention. The illumination devices may also be coupled to the trocar body (12) via flexible attachment members, as described above, such that the illumination devices are bent and covered by the outer housing (32) during the insertion of the trocar assembly (10) into the patient's body.

It would be appreciated by those skilled in the art that various changes and modifications can be made to the illustrated embodiment without departing from the spirit of the present invention. All such modifications and changes are intended to be covered hereby.

What is claimed is:

1. A viewing trocar assembly, comprising:
   a tubular body having a proximal end and a distal end, and an opening provided at the distal end;
   at least one imaging device positioned on an outer circumferential surface of said tubular body adjacent the distal end; and
   an outer housing positioned over said tubular body and axially moveable relative thereto, said outer housing moveable between an inactivated position, in which said housing covers said at least one imaging device and biases said at least one imaging device toward said tubular body, and an activated position, in which said outer housing does not cover said at least one imaging device;
   wherein said at least one imaging device is positioned outside of said tubular body adjacent to the outer circumferential surface of said tubular body when said housing is in the inactivated position, and wherein said at least one imaging device is extended further away from the outer circumferential surface of said tubular body when said outer housing is in the activated position than when in the inactivated position.

2. The viewing trocar assembly of claim 1, further comprising at least one connector attaching said at least one imaging device to the outer circumferential surface of said tubular body.

3. The viewing trocar assembly of claim 2, wherein said at least one connector is extended away from the outer circumferential surface of said tubular body at an angle when said outer housing is in the activated position.

4. The viewing trocar assembly of claim 3, wherein the angle is in the range of from about five degrees to about one hundred and eighty degrees.

5. The viewing trocar assembly of claim 2, wherein said at least one connector comprises shape memory material.

6. The viewing trocar assembly of claim 5, wherein said at least one connector comprises nitinol material.

7. The viewing trocar assembly of claim 1, wherein the at least one imaging device comprises three imaging devices positioned on the outer circumferential surface of said tubular body.

8. The viewing trocar assembly of claim 7, wherein the three imaging devices are positioned circumferentially at a substantially equal distance from each other.

9. The viewing trocar assembly of claim 7, wherein image data generated by each of the three imaging devices is displayed on a display as separate images.

10. The viewing trocar assembly of claim 7, wherein image data generated by each of the three imaging devices is displayed on a display as a single combined image.

11. The viewing trocar assembly of claim 1, wherein said outer housing is moved to the activated position by moving the outer housing in a proximal direction.

12. The viewing trocar assembly of claim 1, wherein outer housing is moved to the activated position by moving said tubular body in a distal direction.

13. The viewing trocar assembly of claim 1, further comprising at least one imaging device positioned in an outer wall of said outer housing.

14. The viewing trocar assembly of claim 1, wherein the distal end of said tubular body comprises a piercing device.

15. The viewing trocar assembly of claim 1, further comprising a piercing member movably disposed inside said tubular body and extending out of the distal end of said tubular body when in an activated position.

16. The viewing trocar assembly of claim 1, wherein said at least one imaging device comprises a CMOS device.

17. The viewing trocar assembly of claim 1, wherein said at least one imaging device comprises a CCD device.

18. The viewing trocar assembly of claim 1, wherein said at least one imaging device comprises at least one illumination device generating light for illuminating surrounding tissue.

19. The viewing trocar assembly of claim 18, wherein the at least one illumination device comprises at least one light emitting diode.

20. The viewing trocar assembly of claim 1, further comprising a processor coupled to and receiving image data from said at least one imaging device.

21. The viewing trocar assembly of claim 20, further comprising a display coupled to the processor and displaying image data received from said at least one imaging device.

22. The viewing trocar assembly of claim 20, wherein said processor includes a wireless interface for receiving the image data generated by said at least one imaging device.

23. The viewing trocar assembly of claim 20, wherein the image data generated by said at least one imaging device is transmitted to said processor via a cable.

24. The viewing trocar assembly of claim 1, further comprising a power source providing electrical power to said viewing trocar assembly.

25. The viewing trocar assembly of claim 1, further comprising a storage coupled to said viewing trocar assembly for storing image data generated by said at least one imaging device.

26. The viewing trocar assembly of claim 1, further comprising at least one imaging marker positioned on the outer wall of said tubular member.

27. The viewing trocar assembly of claim 1, further comprising a control device for manipulation of said viewing trocar assembly by a user.

28. A viewing trocar assembly, comprising:
a tubular body having a proximal end and a distal end, and an opening provided at the distal end, the distal end of said tubular body having a pointed shape for puncturing tissue;
at least one imaging device positioned on an outer circumferential surface of said tubular body adjacent the distal end;
an outer housing positioned over said tubular body and axially moveable relative thereto, said outer housing moveable between an inactivated position, in which said housing covers said at least one imaging device and biases said at least one imaging device toward said tubular body, and an activated position, in which said outer housing does not cover said at least one imaging device;
wherein said at least one imaging device is positioned outside of said tubular body adjacent to the outer circumferential surface of said tubular body when said housing is in the inactivated position, and wherein said at least one imaging device is extended further away from the outer circumferential surface of said tubular body when said outer housing is in the activated position than when in the inactivated position.

29. The viewing trocar assembly of claim 28, further comprising at least one connector attaching said at least one imaging device to the outer circumferential surface of said tubular body, wherein said at least one connector comprises shape memory material.

30. The viewing trocar assembly of claim 29, wherein said at least one connector comprises nitinol material.

31. The viewing trocar assembly of claim 28, wherein the at least one imaging device comprises three imaging devices positioned on the outer circumferential surface of said tubular body.

32. The viewing trocar assembly of claim 31, wherein the three imaging devices are positioned circumferentially at a substantially equal distance from each other.

33. The viewing trocar assembly of claim 31, wherein image data generated by each of the three imaging devices is displayed on a display as separate images.

34. The viewing trocar assembly of claim 31, wherein image data generated by each of the three imaging devices is displayed on a display as a single combined image.

35. The viewing trocar assembly of claim 28, wherein said at least one imaging device comprises at least one illumination device generating light for illuminating surrounding tissue.

36. The viewing trocar assembly of claim 28, further comprising a processor coupled to and receiving image data from said at least one imaging device.

37. The viewing trocar assembly of claim 36, further comprising a display coupled to the processor and displaying image data received from said at least one imaging device.

* * * * *